(12) United States Patent
Diamond

(10) Patent No.: US 9,345,053 B2
(45) Date of Patent: May 17, 2016

(54) SYNOPTIC EMERGENCY CELLULAR DEVICE AND SYSTEM

(71) Applicant: Steven Diamond, Bethlehem, PA (US)

(72) Inventor: Steven Diamond, Bethlehem, PA (US)

(73) Assignee: Steven Diamond, Bethlehem, PA (US)

( * ) Notice: Subject to any disclaimer, the term of this patent is extended or adjusted under 35 U.S.C. 154(b) by 0 days.

(21) Appl. No.: 14/958,361

(22) Filed: Dec. 3, 2015

(65) Prior Publication Data

US 2016/0088661 A1    Mar. 24, 2016

Related U.S. Application Data

(60) Continuation of application No. 14/808,395, filed on Jul. 24, 2015, which is a division of application No. 13/694,629, filed on Dec. 19, 2012, now Pat. No. 9,154,931.

(51) Int. Cl.
*H04W 76/00* (2009.01)
*G06F 19/00* (2011.01)
*H04W 12/06* (2009.01)

(52) U.S. Cl.
CPC ........... *H04W 76/007* (2013.01); *G06F 19/323* (2013.01); *H04W 12/06* (2013.01)

(58) Field of Classification Search
CPC ... H04W 76/007; H04W 12/06; G06F 19/323
See application file for complete search history.

(56) References Cited

U.S. PATENT DOCUMENTS

| | | | |
|---|---|---|---|
| 9,154,931 B2 * | 10/2015 | Diamond | |
| 2009/0205041 A1 * | 8/2009 | Michalske | 726/17 |
| 2011/0151826 A1 * | 6/2011 | Miller et al. | 455/404.1 |
| 2014/0148120 A1 * | 5/2014 | Buck | 455/404.2 |

* cited by examiner

*Primary Examiner* — Brandon Miller
(74) *Attorney, Agent, or Firm* — New River Valley IP Law, P.C.; Michele L. Mayberry

(57) ABSTRACT

A wearable emergency cellular device for use in a medical emergency alert situation includes an application containing synoptic medical information and other user data, a call module for mobile communication with a call center and a display for selectively controlling information displayed on the cellular device. Only the call center is able to input the synoptic medical and selected other information to the device. The cellular device is usable for emergency situations other than medical, such as for personal security at home or for mobile use. Various access methods are described using panel displays for medical or other emergency personnel to access the stored cellular device information. Initiation of user communication with the call center can be activated manually or by the user's voice. Also described are an electronic emergency call system and methods for handling an emergency alert using the emergency cellular device.

20 Claims, 10 Drawing Sheets

SYNOPTIC EMERGENCY CELLULAR DEVICE AND SYSTEM

CROSS-REFERENCE TO RELATED APPLICATIONS

The present application claims priority to and is a Continuation Application of U.S. patent application Ser. No. 14/808,395 filed Jul. 24, 2015, which application claims priority to and is a Divisional Application of U.S. patent application Ser. No. 13/694,629 filed Dec. 19, 2012 (published as U.S. Application Publication No. 2014/0171011 on Jun. 19, 2014 and patented as U.S. Pat. No. 9,154,931 on Oct. 6, 2015), the disclosures of which are incorporated herein by reference in their entireties.

BACKGROUND

There is a growing need, and predictions for an even faster future growing need, for medical services given the number of post-World War II children or "baby boomers" that have and continue to become 65 years or older. This growth in numbers, and its corresponding growth in responsive medical emergency services, is predicted to continue even for the next 20 years. This demographic, along with the increases in medical conditions such as obesity and diabetes, particularly in this age population, will place increased demands on the use of medical facilities and the providing of emergency medical services. These demands particularly, although not exclusively, will come from this aging population due in part to their statistical proneness to cardiac and stroke emergencies.

At the same time, "senior citizens" today are more mobile than ever, maintaining active lifestyles, for longer, than their prior generations. It is to the advantage of this baby boomer generation particularly, and desirable that they have access to an emergency apparatus that allows a person to respond to an emergency. Moreover, such an emergency device should not inhibit, intrude upon or restrict a person's active and mobile lifestyle, yet it still must be readily accessible given the unpredictable nature of when, or even if, a medical emergency situation will occur. In other words, the device and its functionality should be portable as well.

SUMMARY OF THE DISCLOSURE

This disclosure teaches an emergency cellular device, an application (APP) for use with such a device, an emergency cellular alert system, and methods for performing an emergency response and for using an emergency cellular device.

The disclosure teaches a small size emergency cellular device suitable to be worn indiscriminately on the person so to provide a mobile emergency alert quickly and conveniently at the onset of an emergency event.

In one embodiment an emergency cellular device makes available to emergency responders vital information needed to deal with the emergency at hand, without giving "overload" of information.

In another embodiment, a synoptic information key is provided to the user to enhance a response to an emergency. Additionally, an emergency alert system using the emergency cellular device whereby a call center is able to notify emergency responders of the event and to most efficiently provide necessary information to the responders.

In another embodiment, an emergency cellular device has an application containing user information that includes synoptic medical information, a memory storage for electronically storing information, a call module comprising a transmit-receive unit configured to transmit a wireless emergency signal comprising identifying information from the cellular device to a call center and receive a confirming wireless response signal from the call center, and a touch screen for selectively displaying the user information, and a display module for controlling information for display on the touch screen, wherein the cellular device is configured to receive and download the application and any updates thereto from the call center.

In another embodiment, the cellular device is configured so that receipt of the confirming wireless response signal causes a menu of the user information to be displayed on the touch screen and the user information to be available for viewing. Other embodiments include a responsive confirm signal that triggers in the cellular device a transmission of the user information to the call center; the call module comprises an emergency button that upon being depressed transmits the emergency signal.

In another embodiment, the cellular device may be configured so that receipt of the confirming wireless response signal activates a digital voice signal for broadcast from the cellular device.

Further, the cellular device can be configured so that receipt of the confirming wireless response signal activates an audible signal that is repeatedly broadcasted at a predetermined time interval from the cellular device. A menu is displayed on a touch screen of the emergency cellular device that contains at least one of user information categories from the group of personal data, medical diagnoses, drugs and vaccinations/allergies, and the content of a selected one of the user information categories is displayed on the touch screen upon a touch on the touch screen of the selected one of the at least one of user information categories in the menu.

In another embodiment, a microphone and a voice activation unit can be operationally connected to the call module that is configured to transmit a user's voice received at the microphone and the identifying information as the wireless emergency signal transmitted to the call center. The sending of the wireless emergency signal from the cellular device, the display module can cause a key pad to be displayed on the touch screen, with the key pad configured to display the user information upon entry of a code into the cellular device using the key pad. A memory storage of the device contains stored biological markers comprising at least one from the group of a finger print and an iris scan of the user. In this embodiment, displayed predetermined information contains at least one biological marker icon corresponding to the stored biological markers comprising at least one from the group of a finger print and an iris scan, and access to and a display of the user information is obtained by an input of a matching one from the group of a finger print and a iris scan to a corresponding one of the said at least one from the group of a finger print and an iris scan.

In another embodiment of the disclosure, an application is adapted for being downloaded into an electronic device and run on a compatible operating system for communicating information including medical information and synoptic medical information and when run on a compatible operating system, the application displays a numeric pad for entry of an access code, or voice activation for entry of a security access code. Entry of a numeric number, touch of an entry on the touch screen on a displayed menu screen, or use of voice as an audible signal to designate a selected item in the menu, produces a display of the selected information.

In yet another embodiment, an electronic emergency call system has a call center, an emergency rescue communication center operationally connected with the call center, and an emergency cellular device comprising an application sent, and received at the cellular device, from the call center. The application is configured to display synoptic medical information following activation of an emergency wireless call signal by a user of the medical cellular device and transmitted to the call center, and the call center communicates with the emergency rescue communication center to commence a physical response to a site of the medical cellular device.

In one embodiment, the synoptic medical information is displayed at the call center, and as another feature the synoptic medical information is displayed on a touch screen on the medical cellular device.

In still another embodiment, there is presented a method for communicating emergency medical information that includes the steps of downloading an application containing synoptic medical information sent from a call center to a medical cellular device, said medical cellular device being wearable on a user of the medical cellular device, sending an emergency call signal activated by the user from the medical cellular device to the call center, notifying an emergency rescue communication center of a medical emergency situation at a location of the medical cellular device and conveying related user information from the call center, and responding by emergency rescue personnel to the location of the medical cellular device pursuant to the conveyed related user information.

Other technical features, variations and applications may be readily apparent to one skilled in the art from the following figures, descriptions and claims.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The disclosure will be more particularly described in conjunction with the following drawings wherein.

DETAILED DESCRIPTION OF EMBODIMENTS

Emergency Cellular Device Components

Figure 1:
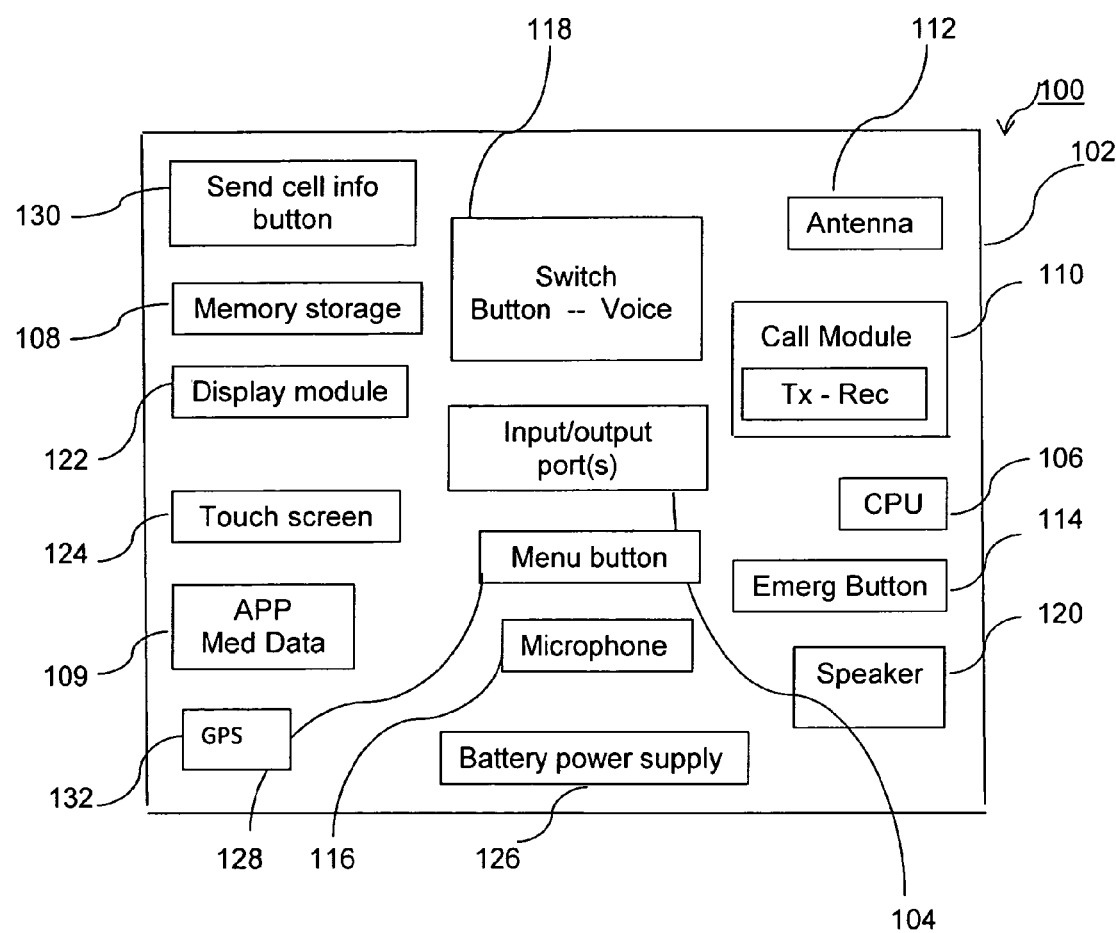
FIG. 1 is a diagram illustrating the emergency cellular device and its primary components.

FIG. 1 illustrates an emergency cellular device 100 and its primary components. The emergency cellular device (also referred to at times herein as "cellular device" and "device" for simplicity) has an outer housing 102 that can be made of any material suitable for housing components and connections of the cellular device. Although shown as being a square or rectangular shape, the housing of the cellular device can be of any shape. The housing shape is relevant especially to any intended mounting of the device such as in a piece of jewelry, discussed later.

The cellular device contains input/output ports 104 as necessary to enable selected functions available with the cellular device, also to be discussed later. A central processing unit (CPU) 106 performs the signal processing and switching functions as part of its overall processing and control of the emergency cellular device's operation. Part of this control is with regard to data stored in the device's memory storage 108 where data is stored in files according to subject matter, such as a user's synoptic medical condition or history, prescribed drugs and allergies of the user, contact information of family and others, and the like.

A call module 110 contains transmit and receive units, or a transceiver, for establishing and using a radio frequency (RF) communication channel between the user and a call center. The call center could be a communication facility associated with a particular hospital, or any other such facility the cellular device is associated with for its operation. Operationally connected to call module 110 is antenna 112.

Emergency button (Emerg button) 114 is a button that the user presses, pushes or depresses to activate the sending of an emergency alert signal to the call center. Microphone 116 is used for the user to be able to speak to the call center as a part of the responsive sequences to the transmission of the emergency alert signal.

Switch 118 is used for the user to set the cellular device for either a manual or voice-activated operation in terms of activating the sending of the emergency alert signal. In the manual position, the signal is activated by the pressing of Emerg button 114. In the voice position, the signal is activated by the user's voice, such as by yelling the word "help", or the like, which is picked up by microphone 116, and the audio signal arrives at CPU 106 where the signal is processed and a signal for transmission is generated from call module 110 and radiated out as a transmitted signal from antenna 112. The microphone in one embodiment is maintained in an ON state after the emergency alert signal is transmitted until such time as the cellular device is turned off by disconnecting its battery power. This continually-on function allows the call center to continue to monitor any audible sounds or statements during the time of the emergency situation so to enhance the awareness and monitoring of the situation at the call center. In an alternative embodiment, the microphone is turned off when the communication channel established between the call center and the user with the cellular device is terminated after the initial emergency signal is received and any follow-up communication between the two parties to the communication is completed.

Speaker 120 projects outwardly an audible signal from a converted received electronic signal from the call center. Speaker 120 through with the call center audibly communicates to the user, and microphone 116 through with the user communicates with the call center, make up the two way communication that is enabled between the user and the call center after transmission of the emergency alert signal.

Display module 122 in cooperation with CPU 106 controls the display of templates and data files stored in the cellular device. This display is projected on a touch screen 124, which also serves as a switch assembly in that information is selected and displayed by the touching of the screen on a selected text, a computer icon, symbol, or the like. The device is powered by a battery power supply 126. An on-off switch (not shown) could be added to connect and disconnect the power supply. Alternatively, the device can become activated with power when the battery supply is connected, and turned off by simply disconnecting or removing the battery, which conserves space on the small size as contemplated for the emergency cellular device by not using a manual on-off switch component.

It is understood that the identified components are operationally connected within the emergency cellular device and are connected to input and output connectors or ports as used in various options available for the emergency device, as further discussed shortly with reference to input/output port 104.

Emergency Alert System

Figure 2:
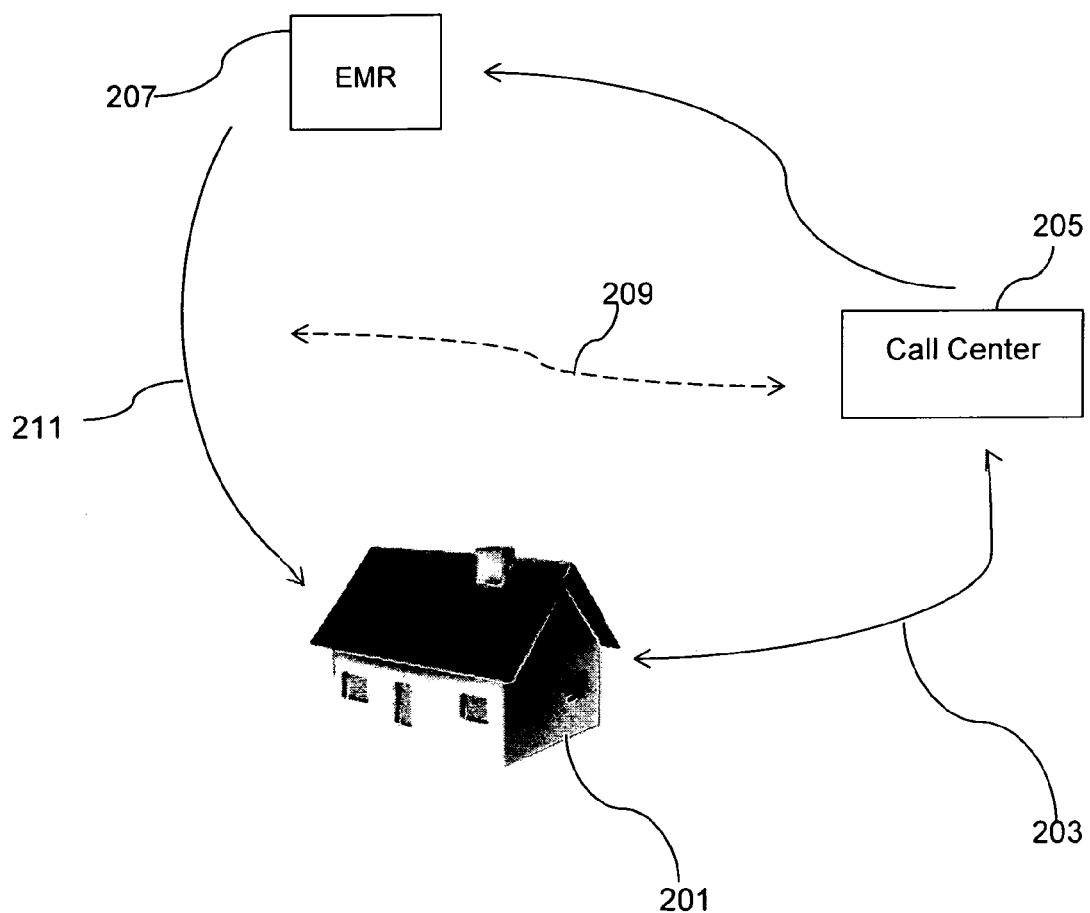
FIG. 2 is a schematic illustration of an emergency alert system using the emergency cellular device.

FIG. 2 is a schematic illustration of an emergency alert system using the emergency cellular device. In a system contemplated for use of the emergency cellular device, a user is, for example, at a residence 201 with the emergency cellular device activated for a medical emergency situation protective function. The user is in communication with a call center 205 via communication link or channel 203. Channel 203 is used for call center 205 to initially transmit an APP containing data relevant to the particular user to the emergency cellular device for downloading into the device. Channel 203 would thereafter be used for transmission of an emergency alert signal from the user in residence 201 upon occurrence of a medical emergency.

Upon receipt of the emergency alert signal, which identifies the user as the sender, the call center, in one aspect of the disclosure, immediately makes contact with an appropriate rescue station. For the purpose of this description, the rescue station is referred to as an emergency medical responder station (EMR) 207. However, this could be any suitable office for responding to the emergency, such as a hospital's ambulance service. For example, if the cellular device were used in a personal security environment, the emergency responder would be a police department of private security agency office. In another aspect of the disclosure, the call center upon receipt of the emergency alert signal, opens a two-way communication channel 203 with the emergency cellular device for confirmation of an emergency situation and to obtain any additional information from the user as appropriate.

After the call center has notified EMR 207 of the emergency, a responding unit is dispatched and proceeds to residence 201, as indicated in FIG. 2 by directional line 211.

While en route, call center 205 is able to communicate further with the responding unit via a communication link 209, which allows for efficient use of time in communication details known about the situation after the responding unit is immediately dispatched to start the travel to the location of the emergency.

Two additional features are noteworthy. One is that even if the user is not able to communicate with call center 205 after sending the emergency alert signal, the call center is able to communicate back to the user that "help is on its way," or the like, so that receipt of the alert signal is confirmed back to the user and re-assuring words are communicated to the user in view of the situation. The other is that upon activation of the emergency signal, or at a predetermined time thereafter, an audible beep or tone is activated from the emergency cellular device at a preset time interval. This enhances the responding party's ability to locate the device and hence the user quickly upon arriving at the scene, being residence 201 in the exemplary illustration of FIG. 2.

Numeric Keypad and Menu Displays

Figure 3:
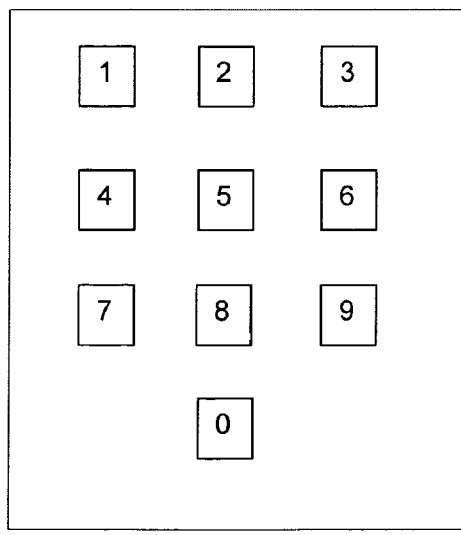
FIG. 3 is a diagram of a numeric keypad as used in the emergency cellular device.

In one embodiment, when the user presses Emerg. button, in addition to the sending of the emergency alert signal, the pressing of the Emerg. Button causes a numeric keypad, such as shown in FIG. 3, to automatically appear on the touch screen. While use of Emerg button 114 is described in this example, the alert signal could also be sent by voice activation if the user selects to put switch 118 in the voice mode.

The call center gives the EMR the emergency cellular device's access code, this being done either at the time of the call center's original call to EMR or while talking en route while EMR is on its way to the user's address. EMR inputs the access code using the displayed numeric keypad upon its arrival at the emergency location to open and view stored information, and in particular the synoptic medical data on the device.

Figure 4:
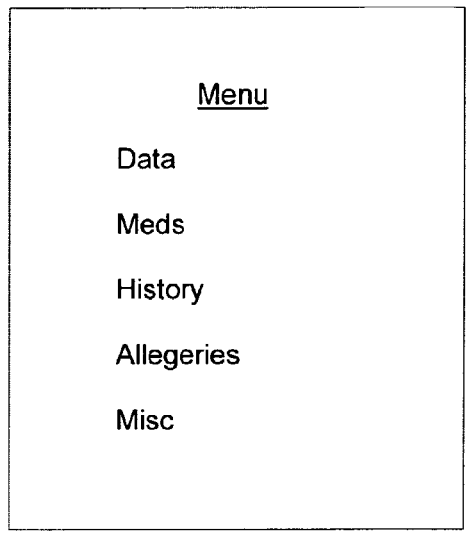
FIG. 4 is a menu screen display according to one embodiment.
Figure 5:
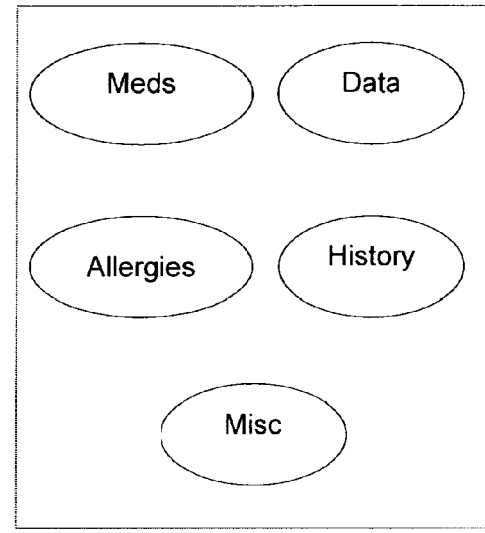
FIG. 5 is another menu screen display according to an alternative embodiment.

FIG. 4 is a menu screen display according to one embodiment, and FIG. 5 is another menu screen display according to an alternative embodiment. FIGS. 4-5 illustrate exemplary menus that can be used to appear on the touch screen when the correct security access code is entered. FIG. 4 presents text headings of the different data that are available in the menu. FIG. 5 shows a format where the individual data files are indicated by icons or symbols. In both FIGS. 4 and 5, the file is opened by touching the desired text or icon, respectively, displayed on touch screen 124.

Figure 6:
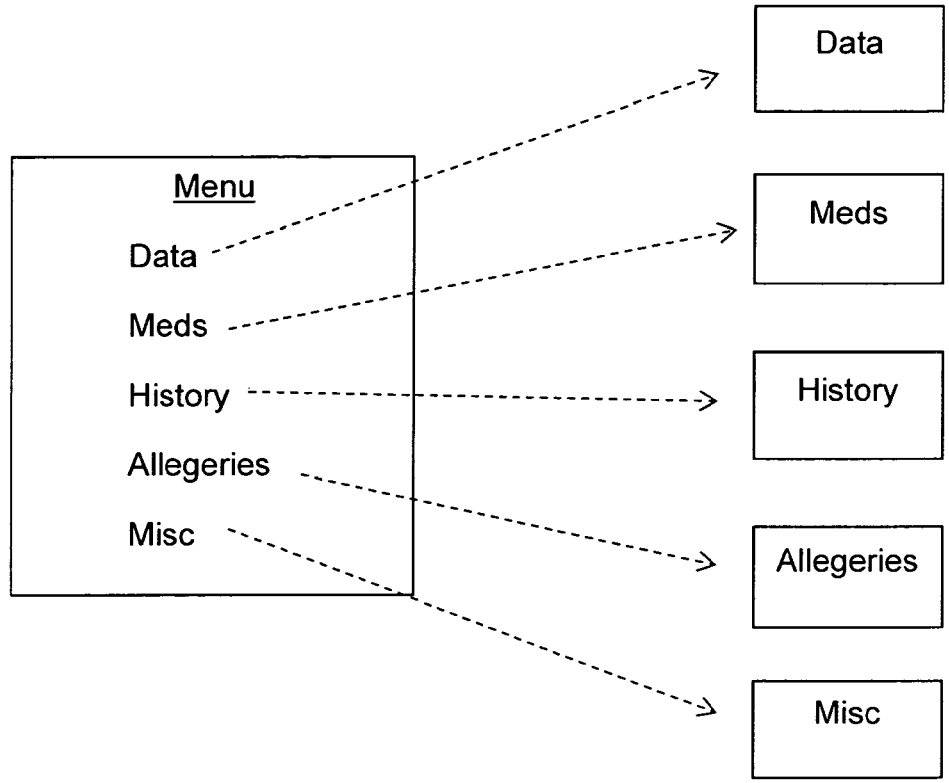
FIG. 6 is a diagram illustrating the opening of specific data folders from the menu screen.

FIG. 6 is a diagram illustrating the opening of specific data folders from the menu screen, and diagrams how individual pages of data are opened under each specific text heading. The same would apply if computer icons were used for the menu instead as in FIG. 5.

Another aspect of the emergency cellular device is its use in a non-emergency situation, such as routine medical visits at a doctor's office, a hospital or at a meeting with a healthcare worker. For this aspect of the disclosure there is another button on the device termed as menu button 128 that is pressed to project a numeric keypad such as shown in FIG. 3 on the touch screen. The user, now perhaps also a patient or client, enters the security code on the keypad to access whatever information is desired with the selection appearing as a menu on the touch screen, whether it be in a text format as in FIG. 4 or in a symbol or icon format as in FIG. 5.

A significant feature of the emergency cellular device is its storage of synoptic medical information. It is synoptic medical information, rather than a full medical history, that is often needed by responders to a medical emergency, as well as being often all that is needed at a medical office visit in that it presents the essential medical information without "overload" or getting into details and history that may not be needed. This enables the user-patient, not in an emergency, but in an urgency or even a routine doctor's visit, healthcare worker visit, pharmacist consult, etc., to show his/her vital information items. This insures that accurate information is conveyed without reliance on memory or having to gather and carry around papers. In the emergency situation, this enables the responders to get quick access to only that medical information necessary for addressing the present situation.

Also preferably only the call center is able to enter, change or even access the synoptic medical information. This provides a higher level of assurance that the synoptic information is correct by blocking others, even the user, from access to this data file. Other data files stored in the emergency cellular device can be similarly blocked, as desired, from access by anyone other than the call center, or left accessible for updates and changes by others, depending upon the setup established for the device.

Touch Screen and Layout Up to Here

Figure 7:
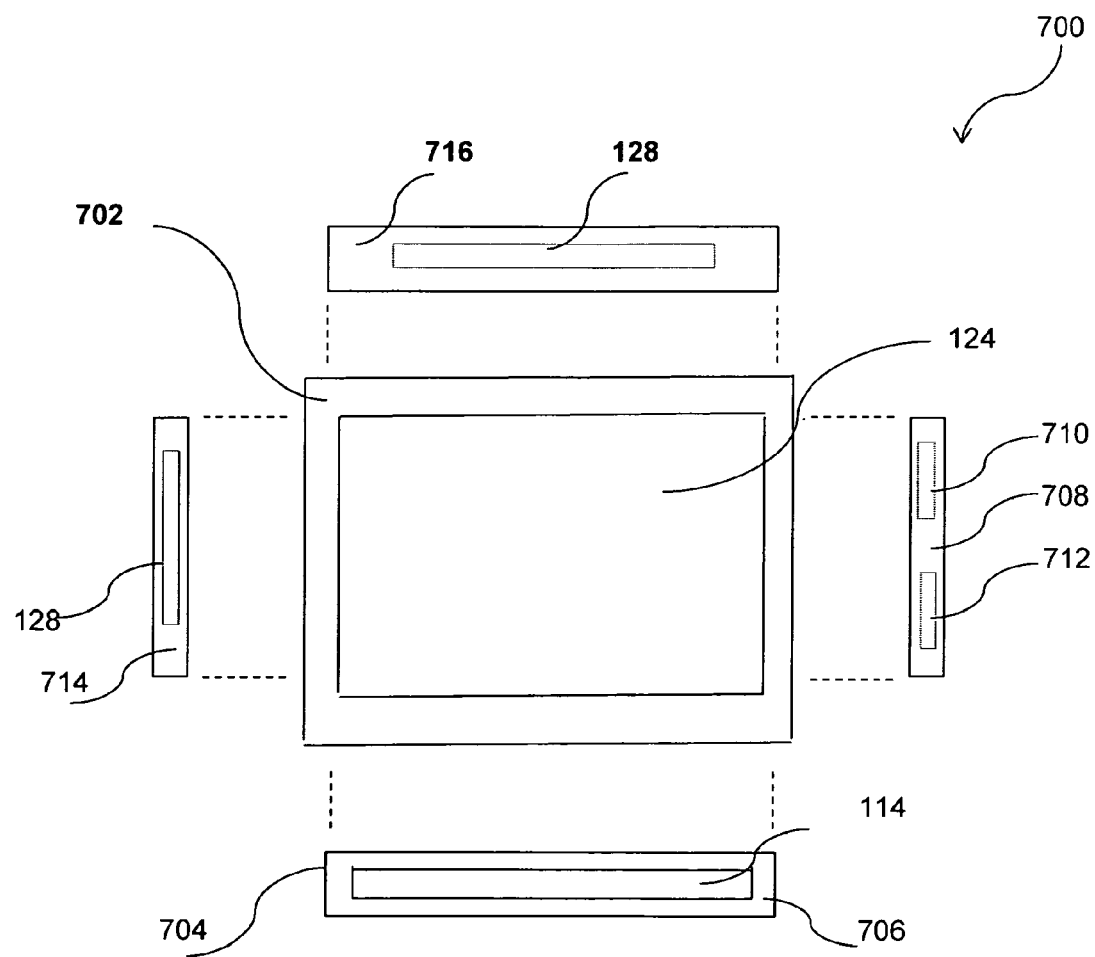
FIG. 7 is a planar view of the touch screen of the emergency cellular device with projected planar view of the four sides according to one embodiment.

Referring to FIG. 7, touch screen 124 occupies the majority of space available on a top surface of the device, thereby enhancing the touch screen's functionality in its use for accessing and viewing information displayed from storage in the device. Touch screen 124 is framed by a border 702 on the top surface.

The dimensions and shapes of the touch screen can be varied from that shown. For example, the projected sides are shown as aligning approximately with the edges of the touch screen rather than the outside edges of border 702. This is just a matter of convenience of illustration and is not intended to indicate a specific size relationship between the top planer surface and touch screen 124 thereon and any of the projected sides shown in FIG. 7. Possible relative size variations include, for example, changes in the widths, lengths and shapes of the sides, the borders, the touch screen and the various connector ports and buttons.

A projected front side of the emergency cellular device is defined by a perimeter 704 wherein emergency button 114 is located. Border 706 lies between an outer edge of button 114 and perimeter 704. The top surface of emergency button 114 extends almost the full length and width of the front side so as to maximize its size for ease in locating it for depressing the button under emergency conditions.

Input-output port 104 (FIG. 1) is located at projected right side 708. This could consist of an arrangement of connections forming a docketing port to connect with a docketing station, or could contain one or more ports as necessary for establishing independent input/output connections.

In one embodiment there is an external microphone (mic) attachment that, when plugged in, disconnects the internal mic 106. A recorder jack is used which when a recorder is connected to it, the audio communications that occur subsequent to the sending of an emergency signal to the call center are recorded. In another embodiment, an external antenna connector is used for connecting an external antenna, automatically disconnecting internal antenna 112, and thereby providing a stronger radiated signal from, and stronger received signal to, the emergency cellular device. In another embodiment, a battery charger port is used for recharging the battery if a rechargeable battery is used in battery power supply 126. In yet another embodiment, the same or another port is provided for use of an external power source to avoid use of the internal battery. This is convenient when the emergency cellular device is used to perform functions in a non-emergency situation, such as printing out data from storage and sending device storage data to the call center. In another embodiment, a port for connecting to an external monitor is added in this input/output port area, in which case internal touch screen 124 is disconnected and the external monitor becomes the display screen.

In one embodiment, at least one USB port is included in input-output port 100 whether used as individual connectors or as a docketing port formed of an arrangement of connections matched for a single connection to a docketing station. The USB ports are used for connecting the emergency cellular device to an external computer or the like. This allows for a print-out of data stored in the device, for viewing the device's data on a larger screen, and/or for inputting data to, or updating data in, the device. In one embodiment, a keyboard, a mouse, external storage, and/or the like is connected as desired to the emergency cellular device at the device's USB ports.

For simplicity of illustration in FIG. 7, only two connectors 710, 712, are shown by way of example as the input/output port module of the device.

Projected left side 714 is located near the menu button 128. Depressing this button brings up the numeric keypad on touch screen 124 and once access is gained to the device, the touch screen is then used as a selector switch for accessing stored information of interest. This is for use generally in non-emergency occasions.

The Send Cell Info button 130 is located near the top side 716. Depressing this button allows the user to transmit selected information to the call center. For example, when the user selects, as an example, the "Meds" menu which then appears on touch screen 124, this information is transmitted to the call center by depressing Send Cell Info button 130. This button overrides emergency button 114 so that the information is sent but not with any emergency situation signal. This feature is helpful, as one example, when the call center wants to confirm or update stored information in the medical cellular device. A hospital, doctor's office or health care facility with a relationship with the user, may have requested information from the call center. The call center uses this feature to obtain the information from the device, or to coordinate the call center's information on file with that stored in the device.

Speaker 120 is in one embodiment, located in border area 702 under a perforated metal or plastic top or the like. Alternatively, speaker 120 is installed any one of the projected bottom, top, right and left sides, 704, 708, 714 and 716, respectively, or any combinations thereof.

Wearable Jewelry

Figure 8:
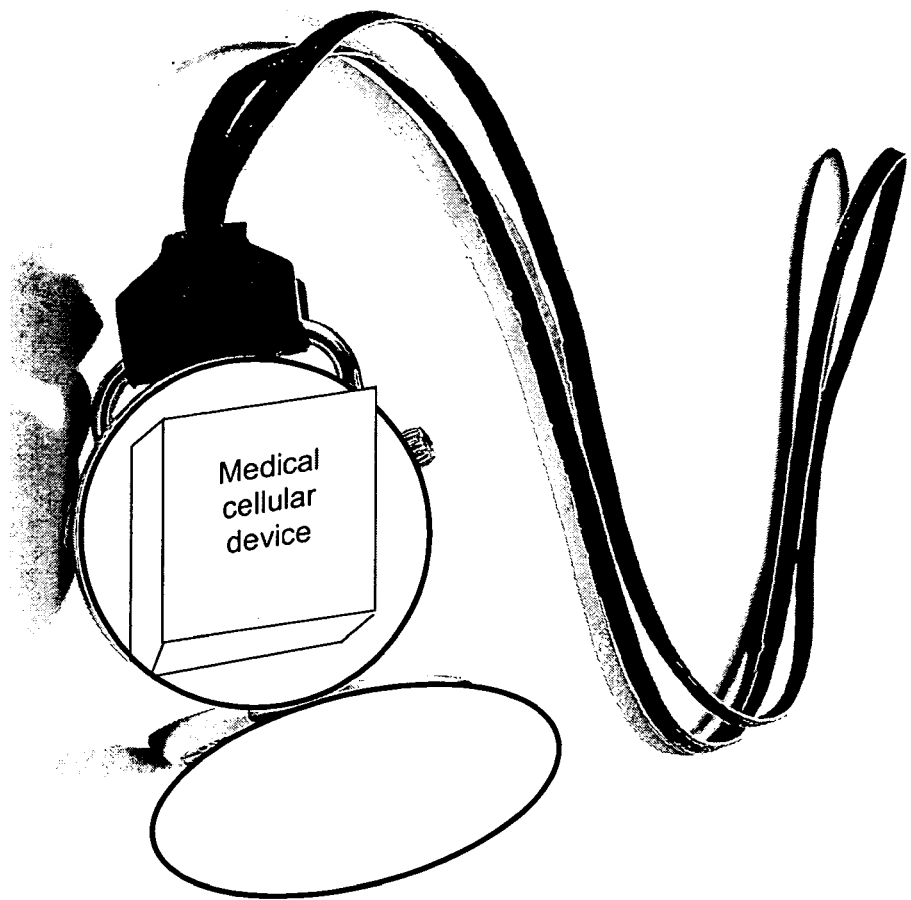
FIG. 8 is a perspective illustration of the emergency cellular device mounted in a wearable piece of jewelry.

Referring to FIG. 8, a wearable receptacle for the medical cellular device is in the form of a piece of jewelry with a hinged or movable cover, illustrated in the open position. The jewelry piece depicted is in the form of a woman's brooch or a necklace or wristlet, with a top moveable surface that covers an inside enclosure of the decorative piece. Such a structure is sometimes used for inserting a picture, a keepsake, or the like, with the enclosure made to be of various sizes as a matter of design choice.

In FIG. 8, emergency cellular device 100 is inserted in such an enclosure which inconspicuously houses the cellular device. The drawing and its components are not necessarily drawn to scale, nor does it represent any particular size, relative sizes or shapes.

Methods of Use

Figure 9:
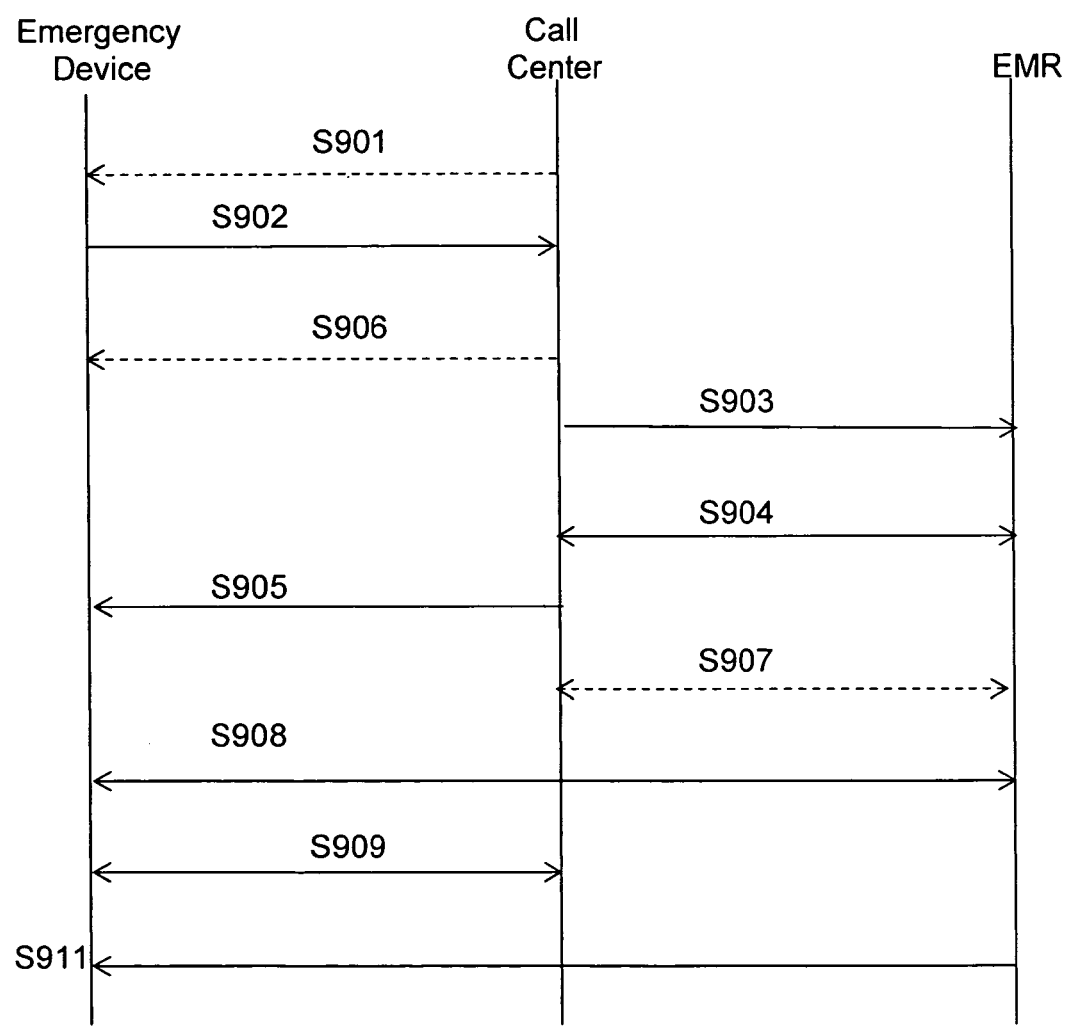
FIG. 9 is a horizontal flow graph illustrating steps in the use of the emergency cellular device according to one embodiment.

Referring to FIG. 9, and prior to user operation of the device, an APP containing synoptic medical data, user profile data, drugs data and other information, as desired, is sent to and downloaded into the emergency device from the call center, as indicated at step S 901. Step S 901 is shown with a dashed line as this is a preliminary step in loading the emergency cellular device and is not a step in the actual use of the device in an emergency event. The call center sends the APP and data contained therein to the emergency cellular device by dialing the number and/or code associated with the emergency device to open a connection or communication channel between the call center and the emergency device.

In one embodiment, the emergency device has an on-off switch for the battery power supply 126. In another embodiment, the no such button in order to conserve space given the small size of the device and given that the device in its use as an emergency alert is most often in an ON state all the time. Since significant battery drain does not occur until the emergency device is actually used, namely, when the emergency button is depressed or voice activator is triggered, the device is able to remain ON in its standby mode without significant battery usage so as to provide a long standby life that could extend for up to 30 days or longer depending on the size battery used as battery power supply 126.

This constant ON condition in a standby mode also allows for the call center to send updates to the APP at any time, such as a synoptic medical data update after an intervening doctor's visit or some other non-emergency medical event, for example.

Referring to FIG. 2, an emergency call is made from the emergency cellular device 100 at residence 201 to call center 205 at the onset of a medical emergency. Step S 902 in FIG. 9. The alert signal is sent by the user pressing emergency button 114 when the device is set for the manual mode, or by an audible sound, such as the user yelling "help," picked up by microphone 116 when the device is set for the voice mode.

While the emergency device is described as having this choice of manual or voice modes for activating an emergency signal to the call center, in one embodiment, the two modes are combined to give a safer backup operating mode. In this combined mode, both the emergency button and the voice activator are active. Thus either pressing the emergency button, OR yelling an audible sound, such as "help" as the word used for this description purpose, will trigger an emergency signal being sent to the call center.

Upon receipt of the medical emergency signal, the call center is able to identify the user from the data received with the signal from the emergency device, such as the sending number or other code. The call center is then able to pull up the information it has on file associated with this user's emergency cellular device. The call center contacts an appropriate office, such as an emergency medical rescue (EMR, #207) station, as indicated at step S 903, to dispatch them to respond to the location of the emergency cellular device. Optionally, the call center and the EMR station can engage in communication as necessary to convey information relevant to the emergency situation at hand, illustrated at step S 904 and dashed line 209 in FIG. 2.

The call center then can communicate, over communication channel 203, back to the user, at step S 905, to, for example, acknowledge receipt of the emergency signal and reassure the user that "help is on its way." Alternatively, the call center can first upon receiving an emergency signal, communicate back to the user to confirm the emergency situation and obtain any additional information that may be available from the user. This alternative is shown by the dashed line of step S 906.

The dashed line of step S 907 illustrates that call center 205 and EMR 207 can communicate with each other while the EMR is en route, #221, to the user's address.

Another option is indicated at step S 908 in that the EMR can also communicate with the user en route (FIG. 2, #211) if desired and if possible, given details of the particular emergency. For example, if the emergency cellular device is set in the voice mode, or in the combined voice-manual mode, the EMR can be patched into the emergency signal communication channel established between the emergency cellular device and the call center so that the EMR continues to hear any audible sounds from the user. In one embodiment, voice communication to the user continues over this channel from either or both the call center as well as the EMR, indicated by the steps S 908 and S 909 in FIG. 9.

Upon arriving at the user's (medical cellular device's) location, the EMR then accesses the medical cellular device, step S 10, and specifically its touch screen to input the necessary security code in order to access the synoptic medical information as well as other information stored in the device in dealing with the nature of the emergency.

Figure 10:
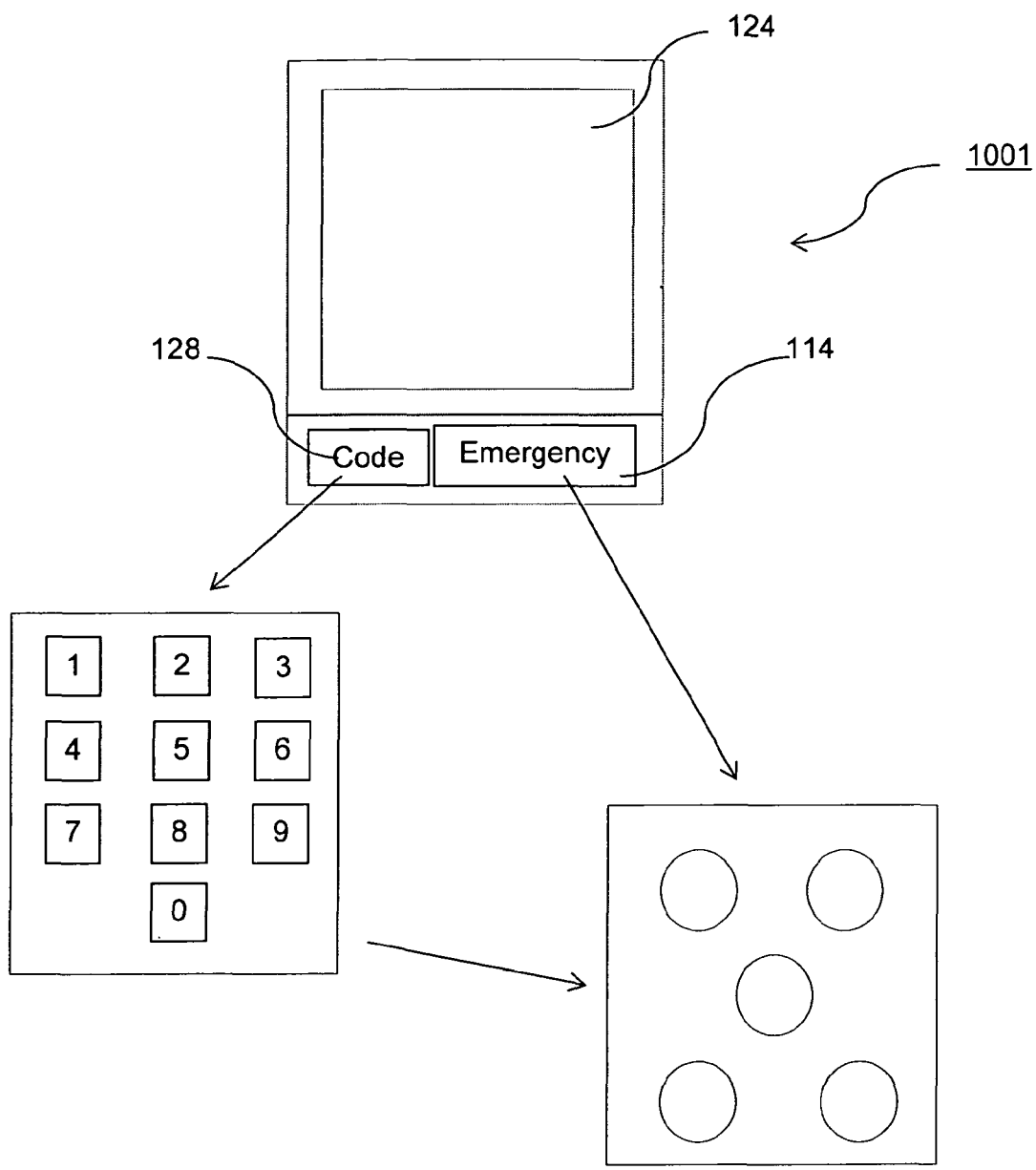
FIG. 10 presents multiple block diagrams showing an alternative embodiment of the touch screen face of the emergency cellular device and its relation to a displayed numeric keypad and an icon display of available data file folders.

FIG. 10 illustrates a touch screen front view of the emergency cellular device and its relation to a displayed numeric keypad and an icon display of available data file folders. This front planar view 1001 is presented of the emergency cellular device in an alternative layout to the embodiment of FIG. 7. Shown in the front planar view is touch screen 124, Emerg Button 114 and menu button 128 (FIG. 1) being shown here labeled as a Code button to reflect its use in pulling up the keypad for entry of an access code. In one embodiment, emergency cellular device 100 functions so that pressing menu button 128 produces the numeric keypad of FIG. 3 which is used to enter an access code to have a menu displayed on touch screen 124, such as a menu arranged with icons, as in FIG. 5, representing the individual data files stored in the cellular device.

In an alternative embodiment, the cellular device functions so that the menu of available data files appears on the display automatically when Emerg. Button 114 is pressed to send the emergency alert signal.

Figure 11:
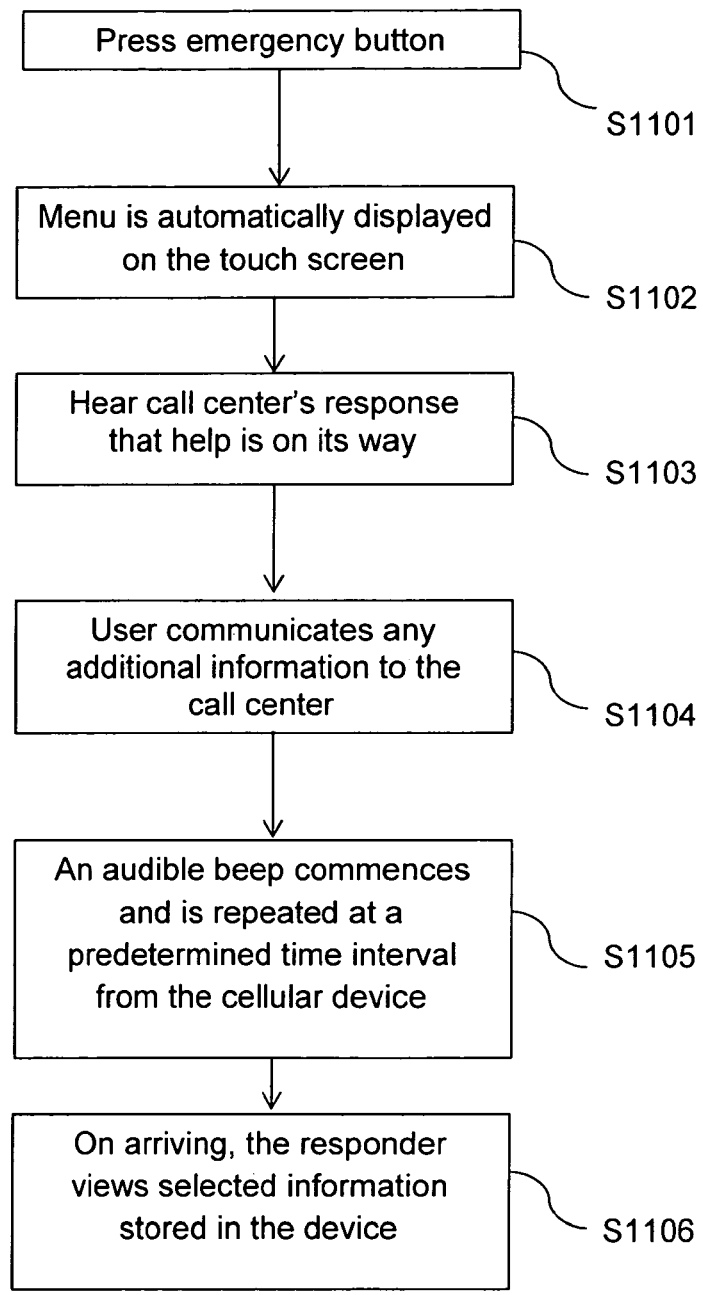
FIG. 11 is a flow chart showing steps in using the emergency cellular device according to one embodiment.

FIG. 11 is a flow chart for a method of use according to one embodiment of the emergency cellular device. FIG. 11 presents a method of use not limited to a particular field of use. Although described with respect to an emergency medical situation as a preferred embodiment of use for the cellular device, the described cellular device is not limited to it functioning in a medical environment. The device, and an emergency alert system incorporating the device, is used in other environments as well. One such application is as a personal security alert device for use at home, at a business or even on the go in a mobile situation.

At step S 1101, a user presses an emergency button on the device at the onset of an emergency situation. In the embodiment of FIG. 11, the pressing of the emergency button both sends a signal to a call center and automatically causes a menu of data available in the device to be displayed on a touch screen, as shown as step 1102. In other words, the pressing of the emergency button overrides the locked access to data in the device that is otherwise not accessible without entry of a security access code, and makes that data available via the menu being displayed. This is considered helpful for either the user or personnel responding to the emergency alert signal to access needed information quickly without having to know, and going through the step of keying in, an access code when time is of the essence.

Next at step S 1103, the user hears the call center's response, such as "help is on its way", or the like, which serves to confirm that the emergency signal was received and is reassuring to the user that help has been summoned.

With a communication channel having been opened between the user and the call center, the user at step S 1104 is able to respond back to the call center audibly with any additional information if desired.

An audible beep or the like is activated from the cellular device so to enhance the locating of the device by responders when they arrive at the location of the device, as shown by step S 1105. This audible tone or beep can be activated when the emergency button is pressed in step S 1101, or when the audible communication ceases between the user and the call center, or at any predetermined point in time, such as starting x number of minutes or seconds after the emergency button is pressed.

In one embodiment, at step S 1106, the one or more responders that arrive on the scene at the location of the cellular device views immediately any information stored in the cellular device to assist them in providing further responsive measures that the information enables them to do.

Figure 12:
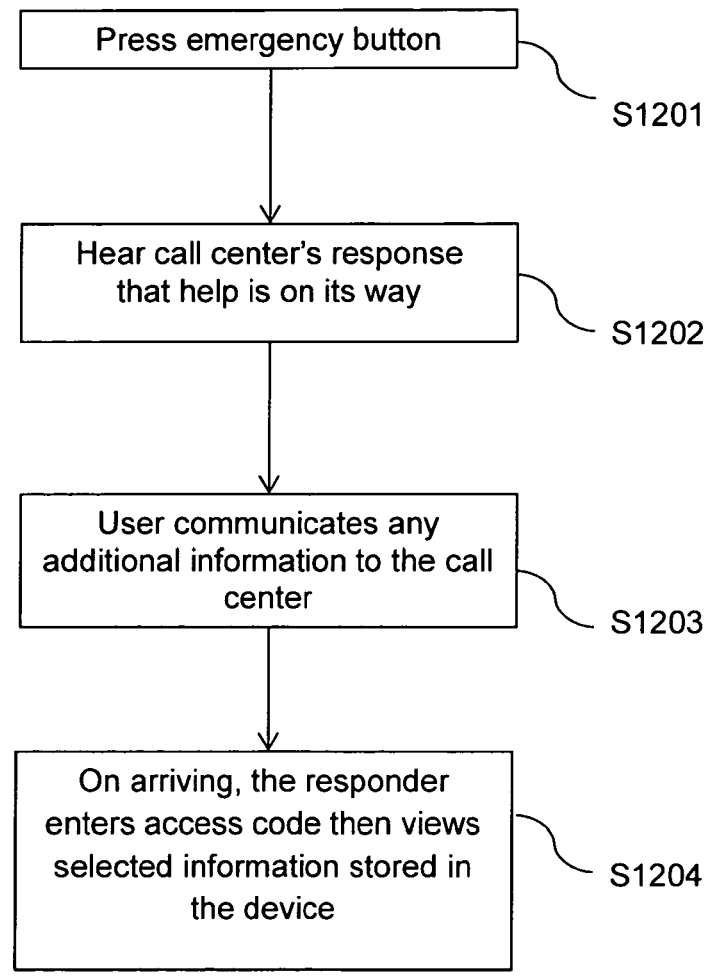
FIG. 12 is another flow chart showing steps in using the emergency cellular device according to another embodiment.

In the embodiment of FIG. 12, the security in terms of accessing the information stored in the cellular device remains intact. Thus when the emergency button is pressed, the menu is not automatically displayed on the touch screen. Steps S 1201, S 1202 and S 1203 are the same as steps S 1101, S 1103 and S 1104 in FIG. 11. (Common steps were not repeated in FIG. 12). At step S 1204, the responder(s), upon arriving on the scene, enter the security access code for the device which brings up the menu, as described with respect to FIGS. 3-6.

Except for this difference in the emergency responders having to enter the security code to gain access to the information stored in the device, the steps of FIG. 12 are the same as those of FIG. 11. Also for simplicity, step S 1105 in FIG. 11 is omitted in FIG. 12. However, the sending of an audible beep from the device is a matter of choice and this step can also be included in the method of FIG. 12 as described with reference to FIG. 11.

Although the descriptions of the medical cellular device, its system and its methods, have been described in various embodiments relating to its use in a medical emergency situation, the disclosed device, its structure and components, and an emergency response system using the emergency device is not so limited. For example, the disclosure is also applicable to security situations where the call center would be a police department or a private security service. The same or similar operating device and its components, the same or similar system interaction and the same or similar methods, steps and processes have application for security and child protective emergency usages as just two examples.

In use of the disclosure as a security measure, the emergency device can be used as a premises security device, such as for a residential/home security or for security at a business premises. Further in terms of its security applications, a user can carry the emergency device inconspicuously on their person, as a wearable piece of jewelry or in a purse according to some exemplary embodiments described herein. This would then serve as a mobile security alert device, with application as well for child security. When used as part of a security system, the responding party would be, the police, personal from a private security firm, or parents, as examples, instead of the EMR.

The embodiments described herein are examples of structures, systems or methods having elements corresponding to the elements of the disclosure recited in the claims. The intended scope of the disclosure thus includes other structures, systems or methods that do not differ from the literal language of the claims, and further includes other structures, systems or methods with insubstantial differences form the literal language of the claims.

The invention claimed is:

1. A medical cellular device comprising:
   (a) a call module, and
   (b) an application containing:
      (i) personal medical information, and
      (ii) a security module for selectively controlling display of the personal medical information on the medical cellular device, wherein:
         the call module is configured to send a transmission signal from the medical cellular device to a call center and to receive a response signal from the call center,
         the personal medical information is stored in a memory storage on the medical cellular device and the application is configured to lock access to the personal medical information,
         upon receipt of the response signal from the call center, a menu of the personal medical information is displayed on the medical cellular device.

2. The medical cellular device of claim 1, wherein the menu comprises at least one category selected from personal data, personal medical condition information, personal medical history information, prescribed drugs, and allergies.

3. The medical cellular device of claim 2, further comprising a touch screen, wherein content of at least one of the categories is displayed on the touch screen upon selection of at least one of the categories in the menu of categories.

4. The medical cellular device of claim 1, wherein receipt of the response signal activates a digital voice signal for broadcast from the cellular device.

5. The medical cellular device of claim 1, wherein receipt of the response signal activates an audible signal from the cellular device.

6. The medical cellular device of claim 1, wherein the personal medical information is available for viewing on the medical cellular device.

7. The medical cellular device of claim 1, wherein the application provides access to the personal medical information through entry of an access code.

8. The medical cellular device of claim 1, wherein the medical cellular device is adapted to transmit the personal medical information to the call center upon receipt of the response signal from the call center.

9. The medical cellular device of claim 1, wherein the medical cellular device is capable of insertion into wearable jewelry.

10. The medical cellular device of claim 9, wherein the jewelry is a brooch, a necklace, or a wristlet.

11. The medical cellular device of claim 1, wherein the memory storage comprises one or more stored biological markers, and the application provides access to the personal medical information through matching of one of the stored biological markers to a biological marker input into the application.

12. The medical cellular device of claim 11, wherein the stored biological marker and the biological marker input into the application is an iris scan.

13. The medical cellular device of claim 11, wherein the stored biological marker and the biological marker input into the application is a finger print.

14. The medical cellular device of claim 1, further comprising a microphone for voice activation of the voice signal.

15. The medical cellular device of claim 1, wherein the call module comprises an emergency button that upon being depressed transmits the voice signal.

16. The medical cellular device of claim 7, wherein the call center is adapted to provide an Emergency Medical Responder the access code after the transmission signal is sent from the medical cellular device to the call center.

17. The medical cellular device of claim 1, wherein individual data files in the menu of the personal medical information are indicated by text headings, symbols, or icons.

18. The medical cellular device of claim 1, further comprising an input-output port.

19. The medical cellular device of claim 18, wherein the input-output port is a USB port.

20. The medical cellular device of claim 1, further comprising a GPS module.

* * * * *